United States Patent [19]

Vinas

[11] Patent Number: 5,041,557
[45] Date of Patent: Aug. 20, 1991

[54] FURAN DERIVATIVES

[75] Inventor: Antonio B. Vinas, Barcelona, Spain

[73] Assignee: Laboratorios Vinas S.A., Barcelona, Spain

[21] Appl. No.: 482,816

[22] Filed: Feb. 21, 1990

[30] Foreign Application Priority Data

Mar. 9, 1989 [ES] Spain .................................. 8900857

[51] Int. Cl.⁵ ........................ C07D 307/52; C07F 3/06
[52] U.S. Cl. .................................... 549/206; 549/495
[58] Field of Search ............................... 549/206, 495

[56] References Cited

U.S. PATENT DOCUMENTS 4,279,819 7/1981 Price et al. ..................... 549/495 X Primary Examiner—Richard L. Raymond
Attorney, Agent, or Firm—Dressler, Goldsmith, Shore, Sutker & Milnamow, Ltd.

[57] ABSTRACT

Furan derivatives of the general formula I

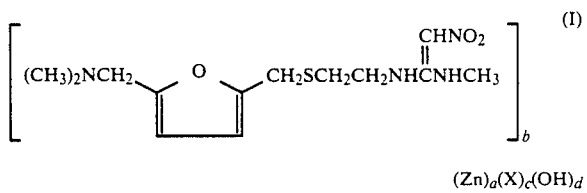

where:
  X is an anion of pharmaceutically acceptable acids;
  a is an integer from 1 to 5;
  b is an integer from 1 to 7;
  c is zero or an integer from 1 to 4; and
  d is 2a–c, for anions of monovalent acids, is a–c, for anions of divalent acids, and is zero or 2, when c is zero, are described as having notable antiulcer properties.

A process for the preparation of said furan derivatives based on reacting N,N-dimethyl-5-(2-(1-methylamino-2-nitrovinylamino)ethylthiomethyl)furfurylamine and an X anion-containing zinc compound or an organozinc is also disclosed.

4 Claims, No Drawings

FURAN DERIVATIVES

The invention relates to furan derivatives of general formula I

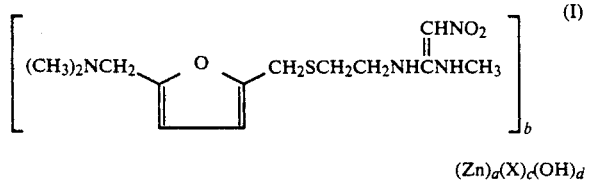

where:
- X is an anion of pharmaceutically acceptable acids;
- a is an integer from 1 to 5;
- b is an integer from 1 to 7;
- c is zero or an integer from 1 to 4; and
- d is 2a-c, for anions of monovalent acids, is a-c, for anions of divalent acids, and is zero or 2, when c is zero.

These compounds have antiulcer properties.

Chronic gastric and duodenal ulcers are frequent disorders for which there is available a wide range of treatments, including dietary measures, surgery and drug treatment. Among the latter, special attention has been paid in recent years to treatment with secretion inhibitors, one of the secretion inhibitors currently on the market being N,N-dimethyl-5-(2-(1-methylamino-2-nitrovinylamino)ethylthiomethyl)furfurylamine, of formula II, supplied in hydrocloride form and hereinafter abbreviatedly called: "Rn".

The said compound Rn has the following structural formula II:

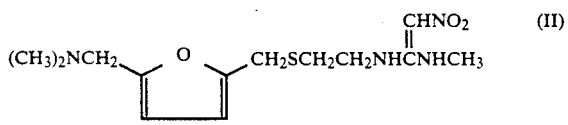

The furan derivatives of the present invention provide advantages on improving the antiulcer properties of Rn.

In the formula I furan derivatives, X may be an anion of pharmaceutically acceptable inorganic acids such as: hydrochloric acid, sulfuric acid, phosphoric acid, hydrobromic acid, hydroiodic acid and others; it may also be an anion of non-toxic organic acids such as: mono- and dicarboxylic aliphatic acids, phenyl substituted alkanoic acids, hydroxyalkanoic acids, alkanodioic acids, aromatic acids, aromatic and aliphatic sulfonic acids and others.

Therefore, X may be chloride, bromide, iodide, fluoride, sulfate, phosphate, chlorate, nitrate, sulfamate, maleate, fumarate, succinate, oxalate, acetate, acexamate, tartrate, citrate, camphorsulfonate, mandelate, butyno-1,4-dioate, benzoate, chlorobenzoate, methylbenzoate, hydroxybenzoate, methoxybenzoate, benzene sulfonate, toluene sulfonate, phenylacetate, salicylate, β-hydroxybutyrate, glycolate, methane sulfonate and the like.

The invention also relates to a process for the preparation of said formula I derivatives.

The process according to the invention is characterized in that N,N-dimethyl-5-(2-(1-methylamino-2-nitrovinylamino)ethylthiomethyl)furfurylamine of formula II is reacted with a zinc compound containing anion X or an organozinc; the proportions of the reactants are variable depending on the type of formula I compound it is desired to obtain.

Preferably said zinc compound is an organic or inorganic anion X-containing zinc salt and the reaction is conducted in a polar organic solvent such as dimethylformamide, dimethylsulfoxide, 1,4-dioxane, tetrahydrofuran, ethyl acetate, acetonitrile, acetone, low molecular weight alcohols, etc. or in an organico-aqueous mixture. An alcohol or ethyl acetate will preferably be used. The reaction temperature may be up to the solvent boiling point but will preferably lie between room temperature and 60° C. Depending on the type of formula I compound it is desired specifically to isolate, and alkaline or alkaline earth hydroxide may be added or not at the end to adjust to an alkaline pH, preferably pH=8. Water may also be added when the reaction has been conducted in an organic solvent alone and an inert atmosphere may also optionally be used, depending on the chosen reaction conditions.

The compounds are obtained in form of a solid or of a thick oil which, after removal of the solvent under vacuum, is converted into a solid, and they may be dried at room temperature or at a high temperature.

To facilitate the understanding of the process for preparing the new compounds of formula I of the invention, it is illustrated but not limited by the following examples.

Example 1: Rn Zn Cl$_2$

A solution of 3.0 g (9.5 mmol) of Rn in 100 ml of absolute isopropanol was added slowly, with stirring over a solution of 1.43 g (10.5 mmol) of anhydrous zinc chloride in 100 ml of absolute isopropanol in a reaction flask (provided with calcium chloride tube and nitrogen atmosphere). When the addition was ended, stirring was continued for 15 minutes. The precipitate was filtered, washed with absolute isopropanol and the residual solvent was eliminated at reduced pressure at 50° C. The precipitate was dried at 75° C. under reduced pressure in the presents of phosphorous pentoxide. A white solid was obtained, the analytical results of which agree with a Rn/Zn/Cl ratio of 1/1/2.

Rn, chromatographic analysis (HPLC): 69.5±2%
Zn, complexometric titration (EDTA): 14.4±0.2%
Cl, potentiometric titration: 15.6±0.2%

| Elementary analysis for $C_{13}H_{22}N_4O_3S \cdot ZnCl_2$: | | | | |
|---|---|---|---|---|
| | C | H | N | Cl |
| Calculated (%) | 34.64 | 4.92 | 12.43 | 15.73 |
| Found (%) | 34.22 | 5.20 | 12.26 | 15.35 |

IR(KBr): 3412, 1624, 1577, 1438, 1388, 1237, 1016, 804 and 758 cm$^{-1}$.

1H NMR (CD$_3$OD+10% CD$_3$SOCD$_3$), δ=2.38 (S, 6H), 2.77 (T, 2H), 2.88 (S, 3H), 3.40 (t, 2H), 3.73 (S, 2H), 3.82 (S, 2H), 4.66 (S, 3H), 6.28 (d, 1H) and 6.35 (D, 1H) ppm.

EXAMPLE 2: Rn Zn I$_2$

A solution of 0.94 g (3,0 mmol) of Rn in 80 ml of absolute isopropanol was added slowly, with stirring over a solution of 1.05 g (3.3 mmol) of anhydrous zinc iodide in 80 ml of absolute isopropanol in a reaction flask (provided with calcium chloride tube and nitrogen atmosphere). When the addition was ended, stirring was continued for 15 minutes. The precipitate was filtered, washed with absolute isopropanol and the residual solvent was eliminated at reduced pressure at 50° C. the precipitate was dried at 60° C. under reduced pressure in the presents of phosphorous pentoxide. 1.40 g of a white solid were obtained, the analytical results of which agree with a Rn/Zn/I ratio of 1/1/2.

Rn, chromatographic analysis (HPLC): 48.0±2%
Zn, complexometric titration (EDTA): 9.85±0.2%
I, potentiometric titration: 39.0±0.2%

| Elementary analysis for $C_{13}H_{22}N_4O_3S \cdot ZnI_2$: | | | | |
|---|---|---|---|---|
| | | C | H | N |
| Calculated | (%) | 24.64 | 3.50 | 8.84 |
| Found | (%) | 24.18 | 3.89 | 8.60 |

IR(KBr): 3415, 1618, 1576, 1464, 1438, 1234, 1015, 801 and 757 cm$^{-1}$.

1H NMR (CD$_3$SOCD$_3$), $\delta = 2.22$ (S, 6H), 2.4–2.9 (complex signal, 5H), 3.1–3.5 (complex signal, 2H), 3.52 (S, 2H), 3.80 (S, 2H) 6.22 (d, 1H), 6.27 (D, 1H), 6.50 (S, 1H), 7.3 (broad band, 1N) and 9.3 (broad band, 1H) ppm.

As stated above, the formula I compounds have shown a potent antiulcer activity. Thus the inhibition of histamine induced gastric secretion "in vivo" in rats, after intraperitoneal administration of these zinc-furan compounds at dose levels of 0.5; 1; 2 and 4 mg/kg reaches pH recovery levels, increasing with the dose, of 100%. The antiulcer activity in the rat against ethanol induced ulcers has shown itself to be satisfactory at dose levels between 50 and 150 mg/kg p.o. and in certain cases complete inhibition of the ulcers has been observed.

The results are given below of tests carried out to evidence the pharmacological activity of the compound Rn Zn Cl$_2$ which will be abbreviatedly called LV-208 hereinafter.

Particularly, the antiulcer activity of the compound LV-208 has been studied with evaluation of the secretion inhibiting and gastric mucous membrane protecting activity in the rat.

A) "In vivo" histamine induced gastric acid secretion model in the rat:

This activity was measured in Wistar rats having a body weight of 240±20 g. An endovenous perfusion of a histamine solution stimulated the gastric secretion producing a drop in the intragastric pH. LV-208 was thereafter administered intraperitoneally and the increase in the gastric pH that this produced was evaluated. An ED$_{50}$ of 0.8 mg/kg and recovery of 100% at a dose of 4 mg/kg was obtained by a dose-response curve.

B) Necrosing agent model:

The activity of LV-208 was compared with the activity of Rn at equimolar doses using the necrosing agent model, ethanol in this case, described by Robert et al. (Gastroenterology, 77: 433, 1979), versus a control group administered excipient.

The following Table gives the lesion indexes (in mm of ulcer) of the three groups studied, as well as the ulcer inhibition percentages of the treated groups versus the control group (mean values±the error of the mean).

TABLE

| | mm lesion | % inhibition |
|---|---|---|
| Control | 82.0 ± 10.1 | — |
| Rn | 40.6 ± 15.0 | 50.5 |
| LV-208 (100 mg/kg) | 4.8 ± 1.8[a,b] | 94.1 | t test: a, $p < 0.001$ versus control; b, $p < 0.05$ versus Rn

As may be seen, LV-208 provides a practically complete protection against the ethanol induced agression, while Rn provides discreet protection at equimolar doses.

What I claim is:

1. Furan derivatives of formula I

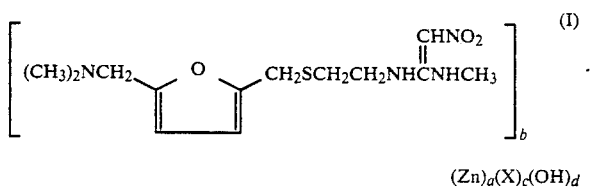

where:
X is an anion of pharmaceutically acceptable acids;
a is an integer from 1 to 5;
b is an integer from 1 to 7;
c is an integer from 1 to 4; and
d is 2a–c, for anions of monovalent acids, and is a–c, for anions of divalent acids.

2.- The derivatives of claim 1, wherein the anion X is selected from the group formed by chloride, bromide, iodide, fluoride, sulfate, phosphate, chlorate, nitrate, sulfamate, maleate, fumarate, succinate, oxalate, acetate, acexamate, tartrate, citrate, camphorsulfonate, mandelate, butyno-1,4-dioate, benzoate, chlorobenzoate, methylbenzoate, hydroxybenzoate, methoxybenzoate, benzene sulfonate, toluene sulfonate, phenylacetate, salicylate, β-hydroxybutyrate, glycolate, methane sulfonate.

3. Furan derivatives having the general formula

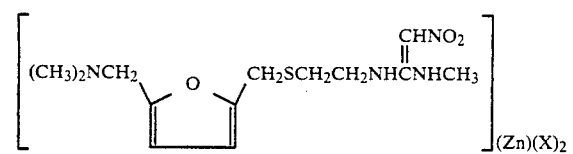

where:
X is an anion of pharmaceutically acceptable acids.

4. Furan derivatives having the formula

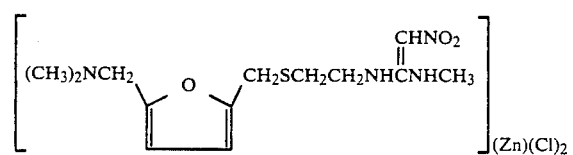

* * * * *